US010820950B2

(12) United States Patent
Uenoyama et al.

(10) Patent No.: US 10,820,950 B2
(45) Date of Patent: Nov. 3, 2020

(54) SERVICE-PROVISION MANAGEMENT SYSTEM

(71) Applicant: RE & DO CO., LTD., Takarazuka (JP)

(72) Inventors: Haruhisa Uenoyama, Takarazuka (JP); Mitsuhiro Uenoyama, Kawanishi (JP)

(73) Assignee: RE & DO CO., LTD, Takarazuka (JP)

( * ) Notice: Subject to any disclaimer, the term of this patent is extended or adjusted under 35 U.S.C. 154(b) by 722 days.

(21) Appl. No.: 15/101,305

(22) PCT Filed: Dec. 11, 2014

(86) PCT No.: PCT/JP2014/082784
§ 371 (c)(1),
(2) Date: Jun. 2, 2016

(87) PCT Pub. No.: WO2015/093382
PCT Pub. Date: Jun. 25, 2015

(65) Prior Publication Data
US 2016/0354165 A1 Dec. 8, 2016

(30) Foreign Application Priority Data
Dec. 20, 2013 (JP) ................................ 2013-263739

(51) Int. Cl.
*A61B 34/30* (2016.01)
*A61G 12/00* (2006.01)
(Continued)

(52) U.S. Cl.
CPC .............. *A61B 34/30* (2016.02); *A61G 12/00* (2013.01); *G06F 19/328* (2013.01); *G06Q 30/04* (2013.01); *G06Q 50/22* (2013.01)

(58) Field of Classification Search
CPC ....... A61B 34/30; G06F 19/00; G06F 19/328; G06Q 30/04; G06Q 50/22; A61G 12/00
(Continued)

(56) References Cited

U.S. PATENT DOCUMENTS

2003/0109960 A1 6/2003 Nourbakhsh et al.
2003/0125987 A1\* 7/2003 Rucker .................. G06Q 10/10
705/3
(Continued)

FOREIGN PATENT DOCUMENTS

JP 2003-339796 A 12/2003
JP 2005-040882 A 2/2005
(Continued)

OTHER PUBLICATIONS

Kazuhiko Kawamura, Cognitive Approach to a Human Adaptive Robot Development, 2005 IEEE International Workshop on Robots and Human Interactive Communication, 2005, p. 629-634, Center for Intelligent Systems/Vanderbilt University, Nashville, Tennessee 37235-0131 USA.

*Primary Examiner* — Robert A Sorey
*Assistant Examiner* — Kimberly A. Sass
(74) *Attorney, Agent, or Firm* — Novick, Kim & Lee, PLLC; Jae Youn Kim (57) ABSTRACT

Provided is a service-provision management system with which the requirements of a large number of users can be fulfilled by a small number of assistants, and with which all of the users can receive services very easily as a result of implementing the highly flexible provision of care and assistance services. The present is provided with: an experience-information data-base which manages experience information related to users (5); and service-provision robots which provide services adapted for the users. The present invention is further provided with: an identification-information acquisition means which acquires user identification information; an experience-information searching means which extracts the experience information related to the users (5); a request identification means which identifies requests of the users (5); a service provision means; and an experience storage means which stores, in the experience- (Continued)

information database, the experience information obtained in accordance with the provision of services.

10 Claims, 4 Drawing Sheets

(51) Int. Cl.
    *G06Q 50/22*     (2018.01)
    *G06Q 30/04*     (2012.01)
    *G06F 19/00*     (2018.01)

(58) Field of Classification Search
    USPC .............................................................. 705/2
    See application file for complete search history.

(56) References Cited

U.S. PATENT DOCUMENTS

| | | | |
|---|---|---|---|
| 2007/0033070 A1* | 2/2007 | Beck | G06Q 10/10 705/2 |
| 2008/0281167 A1* | 11/2008 | Soderberg | A61B 5/00 600/300 |
| 2013/0031010 A1 | 1/2013 | Root | |
| 2013/0158707 A1* | 6/2013 | Lee | G06N 5/02 700/246 |

FOREIGN PATENT DOCUMENTS

| | | |
|---|---|---|
| JP | 2006-235772 A | 9/2006 |
| JP | 2008085421 A | 4/2008 |
| JP | 2011-253389 A | 12/2011 |
| JP | 2013-158386 A | 8/2013 |

* cited by examiner

SERVICE-PROVISION MANAGEMENT SYSTEM

TECHNICAL FIELD

The present invention relates to a service-provision management system, and in particular, relates to a service-provision management system capable of providing services such as care and assistance flexibly in accordance with the needs of the user such as the elderly and the physically handicapped person.

BACKGROUND ART

Conventionally, systems for performing the care and assistance for the user have been conceivable. A user performs an application for a public office so as to receive a service that the user needs, whereby a provision center of care and welfare services has checked the needs of the care assistance, and has requested the dispatch of assistants (helpers) depending on the level of the needed care assistance. However, the number of helpers is limited with respect to the needs of the care assistance, and the situation has occurred that the elderly cannot obtain sufficient care assistance.

On the other hand, the need arises that a helper not only deals with the elderly, but also conducts a work to be a hard work such as walking assistance and bathing assistance of the elderly, and therefore this becomes the cause of the fatigue of the helper himself, and there is also a problem that enough assistance cannot be performed as intended. Thus, in recent years, the use of care robots has been performed so as to reduce the exhaustion of helpers to a minimum. In the following Patent Literature 1 (Japanese Unexamined Patent Publication No. 2013-158386), a robot for performing the standing assistance for a care receiver (user) is described.

Furthermore, in recent years, a special robot for assisting the walking has been used so as to perform the walking assistance for the elderly.

CITATION LIST

Patent Literature

Patent Literature 1: Japanese Unexamined Patent Application Publication No. 2013-158386
Patent Literature 2: U.S. Unexamined Patent Application Publication No. 2013-0031010

SUMMARY OF INVENTION

Technical Problem

By the way, there is a case where especially an elderly person is simply in need of someone to talk to, and when a helper being also someone to talk to moves to the next visiting destination, the elderly person has felt loneliness and anxiety. However, there is a need to meet the needs of a large number of users by a limited number of helpers, and therefore there has been a problem that the helper cannot deal with one user indefinitely.

In addition, as shown in Patent Literature 2 (U.S. Unexamined Patent Application Publication No. 2013-0031010), a system for performing the remote monitoring and the remote management is also conceivable with the cloud database, and it is conceivable to check the state of a user located in a distant place and the like by utilizing this.

However, modern electronic devices are generally very expensive, and if the electronic device is a humanoid robot with such a high degree of artificial intelligence that it can converse with humans, then there is a problem that the robot is not easily available because it is even more expensive, and the robot has not been generalized.

In addition, the elderly person is difficult to adapt to a new hardware, and there is also a problem that the elderly person cannot use the hardware at all if the operation is complicated. Furthermore, in many cases the elderly person has a feeling of rejection against the computer even with a system available in a very simple refined operation, and there is a problem that the elderly person can obtain little benefit of the new technology innovation.

The present invention is made in consideration of the above-described matters, and has an object of providing a service-provision management system capable of satisfying the needs of a large number of users by a small number of assistants and allowing all users to receive services very easily by performing the service provision of highly flexible care and assistance.

Solution to Problem

To achieve the above object, the present invention provides a service-provision management system including: an experience-information database configured to link experience information about a plurality of users to identification information about each of the users so as to manage; a service-provision robot including a service provision means configured to provide a unique service for each of the users so as to provide a service tailored to the user; an identification-information acquisition means configured to acquire the identification information about the user by the service-provision robot coming into contact with each of the users; an experience-information search means configured to access to the experience-information database so as to extract the experience information about the user by using the identification information about the user; a request identification means configured to identify the request of the user by contact with the user; a service provision means configured to provide a service satisfying the request of the user based on the experience information; and an experience storage means configured to store the experience information obtained in accordance with the provision of the service into the experience-information database.

The experience-information database is to be stored in an assistance storage device such as a hard disk provided in an information processing apparatus, and is more preferably a database aimed to be shared by utilizing the cloud computing.

The service-provision robot performs the care and/or the assistance related to the life of the user as service, and it is conceivable that the service-provision robot performs the safety assistance for the user, for example, by attending to the walking training of the user. Besides, it is conceivable that the service-provision robot provides various services, and it is preferable that the service-provision robot includes at least a camera (imaging means). In addition, it is preferable to include arm portions when the services to be provided are those performing some work, and to include a microphone (sound collecting means) and a speaker (sound generating means) when the services to be provided are those performing the dialogue with the user. In addition, the service-provision robot is, more preferably, a humanoid robot (referred to as humanoid or android) formed in the shape imitating a person friendly to the user.

The identification-information acquisition means is to obtain the information for identifying the user, and includes at least one of, for example, a card reader for reading information about the membership card recording the identification information, a keyboard and/or a touch panel for entering the member information, and furthermore, a device that acquires identification information for identifying an individual by the feature identification means for performing the face recognition, the feature analysis, and the like by the image of the user when the service-provision robot includes a camera and a reader of the fingerprint or retinal pattern, and by the feature identification means for performing the voiceprint analysis and the like when the service-provision robot includes a microphone for inputting the speech signal of the user. Although the optimum of the feature identification means is an identification information acquisition program executed by the information processing apparatus in the service-provision robot, the feature identification means may be a device including an identification information acquisition unit constituted by the hardware such as a dedicated IC. Furthermore, the service-provision robot may have a function of transferring the information for obtaining the identification information by the feature identification to a server on the network, and may obtain the identification information by executing the identification information acquisition program to be executed by the server on the network.

The experience-information search means is to extract the information related to the user from the information stored in the experience-information database as the experience information, and the optimum is the experience-information search program to be executed by the information processing apparatus in the service-provision robot. However, the experience-information search program to be executed in the service-provision robot may be the program for generating only search queries such as the SQL to be the search conditions. In addition, the service-provision robot and the like may have the learning function of creating a new query.

The request identification means is to bring out the request of the user, and includes at least one of, for example, a keyboard and/or a touch panel for the user to enter the request, and furthermore, a device that acquires the request by the request identification by the image of the user when the service-provision robot includes a camera, and by the request identification by the speech of the user when the service-provision robot includes a microphone for inputting the speech signal of the user. Although the optimum of the request identification is a request identification program to be executed by the information processing apparatus in the service-provision robot, the request identification may be formed by the hardware such as a speech recognition board. Furthermore, the service-provision robot may have a function of transferring the information for identifying the request by the request identification to a server on the network, and may obtain the request information by executing the request identification program to be executed by the server on the network.

The service provision means is to provide services to be provided to the user, and is conceivable to be the support unit for supporting the body of the user and its control unit when the safety assistance such as the walking training for the user is performed. The service-provision robot is conceivable to include, as the services to be provided, the game match with the user, the provision of food and drink including the service of sake and beer, and work arm and work hand and its control unit when performing the work such as cleaning, and for example, a camera including the pan and tilt control unit and the like, a state determination means for determining the child's state from the child's image, and furthermore, a transmission means for transmitting the information about determining the state of the user onto the network when performing the services such as child protection monitoring.

The experience storage means is to record the experience information obtained in accordance with the provision of services into the experience-information database, and when the user receives the provision of services from the service-provision robot, the service-provision robot stores the experience information obtained in accordance with the provision of services into the experience-information database in association with the identification information about the user. It should be noted that the experience information includes the event information including the communication history with the user such as the request contents of the services made by the user, the questions received from the user, and the promises with the user, and the characteristics information about the user such as the physical characteristics such as the height, weight, and age, the preferences and tastes, and the degree of assistance needed for everyday life.

When the user makes a service request to the service-provision robot, the experience-information search means extracts the experience information about the user by using the identification information about the user acquired by the identification-information acquisition means, and the provision of services suited to the user can be performed depending on the experience information in the service-provision robot. In addition, the experience obtained when responding to the user requests identified by the request identification means is stored into the experience-information database to be used for the next service provision, and therefore even when individuals of the service-provision robot are changed, the provision of the services based on the same experience information can be performed. That is, based on the conversations and promises performed not only when the user first met the service-provision robot, but also at the time of contact with the service-provision robot so far, the provision of additional services is performed, and therefore the user can receive the provision of services while obtaining the nostalgia and a sense of trust, and can obtain a sense of satisfaction as if monopolizing the service-provision robot all the time.

When the service-provision management system includes: a billing database configured to link the billing information, in accordance with the service provision to the user, to the identification information so as to manage; and a billing server on the manager side including a usage fee calculation means for calculating the usage fee by accessing the billing database to extract the billing information, and the service-provision robot or the billing server includes a billing storage means for storing the billing record for the service provision into the billing database, the billing storage means monitors the billing record for the service provision to store the billing information into the billing database, and therefore when the provision of services to the user is performed, the billing information is recorded into the billing database by the billing storage means.

It should be noted that although the billing information means, for example, a fee that occurs with the use of the service-provision management system, the billing information may be the points of services determined in accordance with the needs of the care. The points of services are conceivable that, for example, the billing storage means periodically adds the points determined by the situation of the user, and the points are sequentially subtracted with the use of the service-provision management system. In addition, the points of services may be conceivable to be managed by including the points of not only the services provided by the service-provision management system, but also the services to be supplied by the assistant (helper) visiting the user with the service-provision robot.

In addition, for example, if there is nonpayment of the service usage fee, the service-provision robot may perform the handling such as the maintenance and change of service contents (such as the maintenance and interruption of services and the report that there are arrears) based on the billing information stored in the billing database such that the service-provision robot suspends the provision of services, and for that reason, for example, the billing server and the management apparatus on the manager side may instruct the service-provision robot to perform the handling based on the billing information stored in the billing database, and the service-provision robot may periodically read the billing information about the billing database to perform the handling based on the read billing information.

When the service-provision robot imitates a person of the appearance selected by the tastes of the user, and the experience information includes the taste information indicating the tastes of the user, the appearance of the service-provision robot is selected to suit the preferences and tastes of the user, and the user can treat the service-provision robot with attachment, and have the exclusive feeling of the service-provision robot. The hardware such as the service-provision robot can be shared without being customized to each user, and therefore the cost of equipment can be reduced by that amount.

When the service includes at least one of the conversation with the user, the care for the user, the assistance for the user, the game match with the user, and the provision of food and drink to the user, the provision of services that meet the spiritual needs of the user can be performed. The conversation means the communication with the user by speech, and it is conceivable that the care for the user includes performing the life assistance such as the work such as cleaning and the child protection monitoring, the assistance for the user includes performing the safety assistance for the user by attending to the walking training of the user, the game match with the user includes performing the match such as the card game, the board game such as go and shogi, and the computer game, and the provision of food and drink includes the preparation for food and drink and the service of sake. In addition, the service-provision robot may have a conversation to suit the actions other than the conversation (the care for user, the assistance for user, game match, and the provision of food and drink), and for example, when playing the game match, the service-provision robot may praise the user's skill in the game or lose the game to be chagrined through conversation.

When the service-provision robot has a function of expressing its feelings, the user becomes easier to feel a sense of closeness to the service-provision robot, and becomes easier to receive the care and the assistance by the service-provision robot. In addition, the feelings of the user are easier to be met, and the desire to use it again is enhanced.

For example, when the service-provision robot is a humanoid robot, the function of expressing the feelings is preferable to allow the facial expression to perform the display of expressing at least the feelings, and the service-provision robot is conceivable to include a plurality of actuators and their control units for distorting the skin of the face. Alternatively, when the service-provision robot includes a display unit, the service-provision robot is conceivable to include a feeling display program for displaying the text that expresses the feelings ("(joy)", "(ˆoˆ)/", or the like) or the facial image that represents the facial expressions on the display unit.

When the service-provision robot has a function of movement, the service-provision robot can perform the provision of services by moving to the vicinity of the user in a remote location. In particular, when the walking assistance for the user is performed, the movement function is essential. In addition, even when the service-provision robot is transported to the home of the user by the helper, the service-provision robot includes the movement function, whereby the burden on the helper can be reduced.

When the service-provision robot is a human type robot, the movement function is preferable to include the legs for performing the bipedal walking and their control units. However, the movement function may include a stably movable cart for mounting the service-provision robot.

When the service-provision management system includes a user identification database configured to link at least one of the personal identification number data, the voiceprint verification data, the fingerprint matching data, and the facial image recognition data of the user to the personal information about the user as the user identification data so as to accessibly and systematically manage, and the identification-information acquisition means accesses the user identification database to acquire the identification information about the user, not only the extraction of the personal information can be performed smoothly, but also the reading of the personal information is performed by the features of each user to be recorded into the user identification database, and therefore the protection of the personal information can be performed by that amount.

When the service-provision management system includes a telephone service provision server on the manager side including a telephone connection means for enabling the speech communication and the telephone number communication from the telephone on the user side through the telephone line, the user identification database associates the telephone number of the user with the personal information about the user to manage accessibly and systematically, and the telephone service provision server executes an identification information acquisition program for searching the user identification database by using the telephone number of the user when receiving a call through the telephone line to acquire the identification information, an experience information search program for accessing the experience-information database to extract the experience information about the user by using the identification information about the user, a conversation program for performing the provision of services by the conversation with the user through the telephone line by using the experience information, and an experience storage program for storing the experience information obtained with the provision of services into the experience-information database, the user can have a conversation with the service-provision robot by using the telephone (including mobile telephone) in the feeling of making a call even after the service-provision robot leaves the user.

The telephone service provision server includes a telephone connection means connected to the telephone line, and preferably, a server including the experience-information database is used also as the telephone service provision server. In addition, the telephone connection may be accessibly formed through a network such as the Internet.

The identification information acquisition program is conceivable to obtain, for example, the personal information about the user recorded into the experience-information database and the identification information from the telephone number received by the telephone connection means. Alternatively, the telephone number itself may be set to be the identification information.

The experience information search program and the experience storage program respectively achieve almost the same operations by software as the experience-information search means and the experience storage means.

In addition, the conversation program performs the speech recognition of the speech of the user to enter the reception contents, generates the transmission contents to the user from the reception contents and the experience information associated with the user, and outputs the transmission contents by using the speech synthesis, whereby the conversation program has a conversation with the user by speech, and the conversation contents are transmitted and received through the telephone connection means. Here, the conversation program generates the transmission contents by the experience information extracted by the experience search program, whereby the experience information obtained by the contact of the service-provision robot with the user can be reflected in the conversation.

The telephone number to be connected to the telephone connection means of the telephone service provision server is told to the user at the start of the services or when the service-provision robot visits the user, and when the user makes a call to the telephone number, the identification information acquisition program operates to acquire the telephone number of the user, and based on this, the identification information acquisition program obtains the identification information about the user. The experience information search program extracts the information related to the user from the information about the individual user stored in the experience-information database as the experience information by using the identification information, and the conversation program has a conversation with the user by using the experience information. Therefore, the user can receive the handling as if the service-provision robot previously in contact takes the call to talk together. In addition, the questions, the next promises, and the like are made by the user, and the experience storage program records the experience information obtained by the conversation into the experience-information database. That is, the user has an illusion that he monopolizes the service-provision robot all the time, and can obtain a sense of satisfaction from nostalgia and reliability.

When the service-provision management system includes a net service provision server on the manager side including an Internet connection means for enabling the connection from the terminal on the user side through the Internet, and the net service provision server executes a display program for displaying the image imitating the service-provision robot on the user side terminal by the connection from the user side terminal through the Internet, an identification information acquisition program for acquiring the identification information about the user through the user side terminal, an experience information search program for extracting the experience information about the user from the experience-information database by using the identification information about the user, a conversation program for performing the provision of services by conversation through the terminal on the user side by using the experience information, and an experience storage program for storing the experience information obtained with the provision of services into the experience-information database, the user can meet the service-provision robot again through the Internet, and can have a conversation with the service-provision robot.

The net service provision server includes an Internet connection means connectable with the terminal on the user side through the Internet, and therefore the net service provision server is configured so that the terminal on the user side can be easily connected to the net service provision server. In addition, preferably, a server including the experience-information database is used also as the net service provision server.

It should be noted that the Internet is used in the present description, whereby the provision of services can be received by using the network most widely spread all over the world, and therefore it is preferable; however, the security improvement may be achieved by using a special network such as an intranet. In addition, the terminal on the user side includes not only a personal computer, but also a tablet terminal (PDA) and a mobile telephone terminal.

The display program allows the WWW browser (hereinafter, simply referred to as browser) installed in the terminal on the user side to display an image imitating the service-provision robot, and the service-provision robot is preferable to imitate the appearance of the individual actually visiting the user. In addition, the image of the service-provision robot is preferable to move to suit the contents of the services provided through the browser and the feeling to be expressed.

The identification information acquisition program acquires, for example, any one of the personal information about the user and the physical address of the terminal on the user side recorded into the experience-information database, the contractor unique ID such as the individual identification number and the terminal identification information, the IP address, and the telephone number by the header information and the like, and uses these pieces of information by converting them into the identification information or directly as identification information.

The experience-information-search program and the experience storage program respectively achieve almost the same operations by software as the experience-information search means and the experience storage means.

In addition, the conversation program performs the speech recognition of the speech of the user to enter the reception contents, generates the transmission contents to the user from the reception contents and the experience information associated with the user, and outputs the transmission contents by using the speech synthesis, whereby the conversation program has a conversation with the user by speech, and the conversation contents are transmitted and received by the streaming and the like of the Internet line. Here, the conversation program generates the transmission contents by the experience information extracted by the experience search program, whereby the experience information obtained by the contact of the service-provision robot with the user can be reflected in the conversation.

In addition, it is preferable to integrate the net service provision server with the telephone service provision server and/or the server including the experience-information database so as to form one server, and this enables the sharing of programs to be achieved and the simplification of the system to be achieved.

The URL address of the net service provision server is told to the user when the service starts or the service-provision robot visits the user, and the user enters the URL by the terminal in his hand, whereby the user side terminal can be connected to the net service provision server. In addition, at this time, the identification information acquisition program extracts the information linked to the identification information from the information included in the header information to obtain the identification information.

The experience information search program extracts the information related to the user from the information about the individual user stored in the experience-information database as the experience information by using the identification information, the display program displays the image of the service-provision robot in contact with the user on the user side terminal, and the conversation program has a conversation with the user by using the experience information. Therefore, the user can receive the handling as if the service-provision robot previously in contact takes the call to talk together. In addition, the questions, the next promises, and the like are made by the user, and the experience storage program records the experience information obtained by the conversation into the experience-information database. That is, the user has an illusion that he monopolizes the service-provision robot all the time, and can obtain a sense of satisfaction from nostalgia and reliability.

When the information in the medical institution where the user visits is recorded in the experience-information database, and the service-provision management system includes a user monitoring report means for monitoring the service provision to the user and for detecting the abnormality occurrence to report to the medical institution where the user visits when at least the response of the user is delayed beyond the set threshold value, and when the health situation of the user is suddenly changed, this can be detected as soon as possible to be reported to the medical institution, and therefore the safety is increased by that amount.

The user monitoring report means is preferable to be, for example, the monitoring report program to be executed by the arithmetic processing unit in the service-provision robot. Alternatively, when the telephone service provision server and the net service provision server are disposed, the user monitoring report means is preferable to be the monitoring report program to be executed by these servers. The monitoring report means includes, for example, a timer measured from the service provision time, and a report means for determining the case where the period measured by the timer exceeds the contents of the provided services and the threshold value defined for each user as an abnormal situation so as to report to the contact address recorded as the information in the medical institution. It should be noted that the information includes at least one of the telephone number as the contact address, the mail address, and the information such as the address of the management server used by the medical institution, and the report means includes the communication means for performing the communication to suit the information in the medical institution.

In addition, although when the monitoring report means is disposed inside the individuals performing the service provision such as the service-provision robot, the telephone service provision server, and the net service provision server, the provision situation of the services can be directly monitored, the monitoring report means can be disposed apart from the individuals performing the service provision, and in this case, is a monitoring report program to be executed inside the server accessible to the experience-information database. By monitoring the service provision (in particular, conversation) to the user to be recorded into the experience-information database, the period from the provision time of the services to the response by the user is measured, and when this exceeds the threshold value, the report is made to the medical institution.

When the service-provision management system includes an assistant database where a plurality of assistants are recorded together with their characteristic information, a terminal on the assistant side operable by each of the assistants, and a remote service provision server configured to execute an assistant selection program for searching the assistant database to select the assistant when receiving a request from a user, a personal information transmission program capable of transmitting at least one of the speech and/or the image of the user, the experience information about the user, and the request to only the terminal of the selected assistant, a speech image conversion transmission program for converting the speech information and/or the image information entered through the terminal on the assistant side into the tone and/or the image of the service-provision robot to subsequently transmit to the user, and an experience storage program for storing the input information about the service provision contents by the assistant into the experience-information database as the experience information, the assistant (helper) in a remote location can have a conversation with the user.

The assistant database is preferably a database aimed to be shared by utilizing the cloud computing, and the characteristic information is preferable to include the information such as the hometown (dialect) of the assistant. The remote service provision server is formed to be connectable to the terminal on the user side through the network such as the Internet or the telephone line, and configured to be accessible to the experience-information database as well as the assistant database.

The assistant selection program selects the personal information about the user (such as the information about his hometown with a dialect) from the experience-information database when receiving a request from the user, and the best assistant from the characteristic information about the assistants recorded in the assistant database.

The personal information transmission program transmits at least one of the speeches and/or the image of the user, the experience information about the user, and the request to the terminal of the selected assistant, whereby the assistant can check the state of the user, and perform the provision of services that meet the request of the user. The provision of services is optimally a conversation. In addition, the personal information about the user transmitted to the assistant is preferred to also include the experience information obtained by the previous service provision (situation information such as the promises and the questions with the user and the checking into and out of the hospital of the user), and the assistant is preferable to be able to have a conversation with the user while looking at these personal information.

The speech conversion transmission program converts the speech information to be input through the terminal on the assistant side into the tone of the service-provision robot visiting the user usually to subsequently transmit to the user. In the same way, the image of the assistant (display of the facial expressions and movements) is also preferable to be converted by imitating that of the service-provision robot with a usual visit.

Advantageous Effects of Invention

According to the service provision system with the above configuration, the service provision to the user can be performed by the service-provision robot, and therefore this enables the assistants insufficient in number to be compensated so as to perform the provision of sufficient services to the user. In addition, the user can be connected to the service-provision robot at any time, and therefore can obtain a sense of satisfaction as if monopolizing the service-provision robot. The manager of the service provision system can perform the provision of services to a plurality of users by using a relatively expensive service-provision robot, the cost of equipment can be reduced.

DESCRIPTION OF EMBODIMENTS

In the following, embodiments of the present invention will be described with reference to the drawings.

Figure 1:
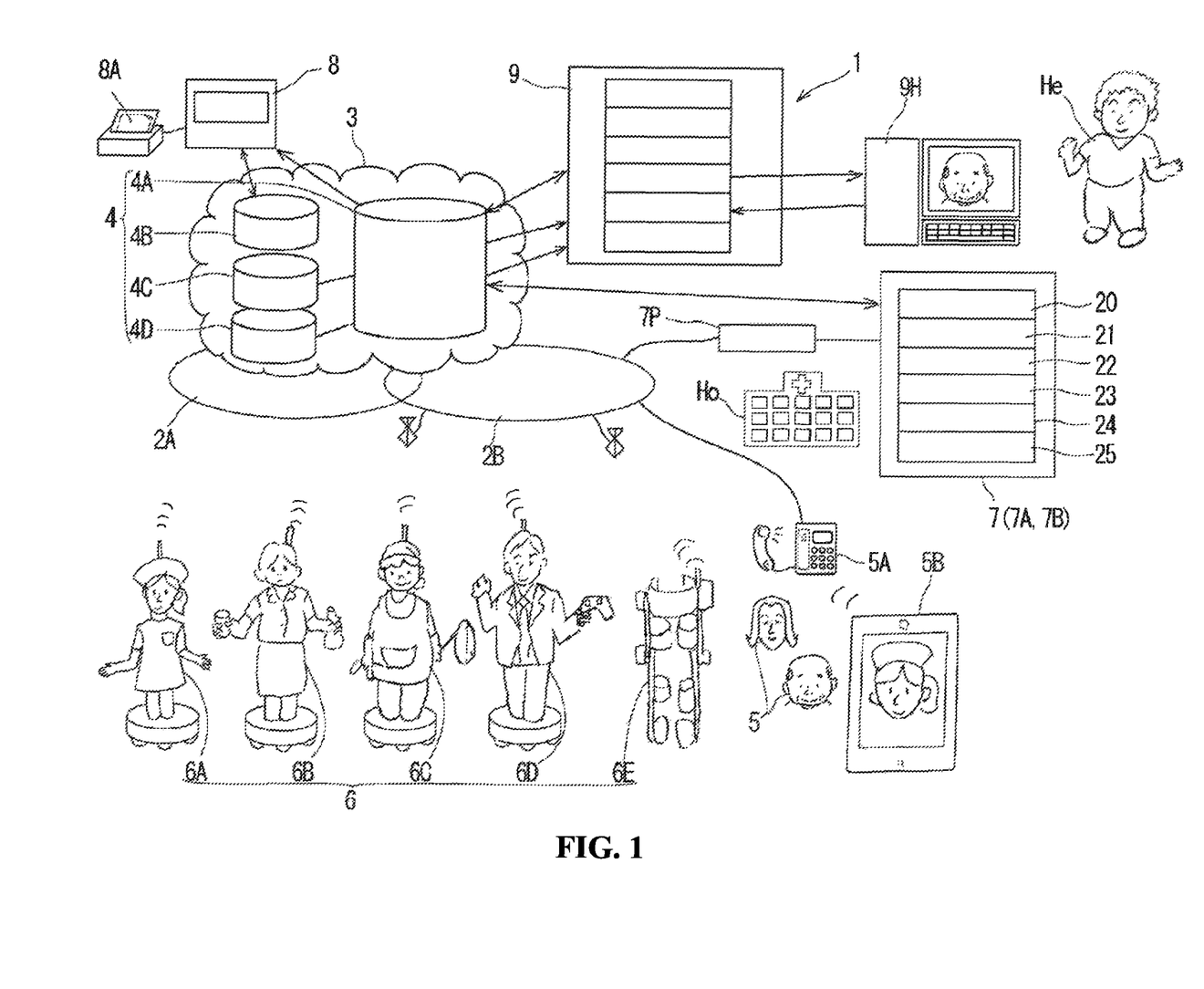
FIG. 1 is an explanatory diagram schematically illustrating the whole of a service provision system according to an embodiment of the present invention.

As illustrated in FIG. 1, the service provision system 1 according to an embodiment of the present invention includes a plurality of databases 4 by using a cloud database 3 (hereinafter simply referred to as cloud 3) formed by the cloud computing on a network such as the Internet 2A, and provides a service using a service-provision robot 6 to a plurality of users 5. It should be noted that the Internet 2A is a widespread and accessible network also connected to the telephone network 2B including a cellular phone, and it is obvious that if there is another accessible network, even a network such as an intranet can be used.

In addition, the service provision system 1 of the present embodiment is configured so that the user 5 can also receive a service without going through the service-provision robot 6 by using a plurality of servers 7, 8, and 9; and the server 7 has both functions of a telephone service provision server 7A for performing a service by phone and of a net service provision server 7B for performing a service by network connection, the server 8 has a function as a billing server, and the server 9 has a function as a remote service provision server.

It should be noted that 7P denotes a telephone connector for performing transmission and reception of a speech signal to and from the user 5 by the connection of the telephone service provision server 7A to the telephone network 2B, 9H denotes an assistant side terminal used by an assistant He (hereinafter referred to as "helper He"), and Ho denotes a medical institution where the attending physician whom the user 5 regularly visits is present.

The database 4 includes, for example, an experience-information database 4A for linking the experience information about a plurality of users 5 to the identification information about each of the users 5 so as to manage, a billing database 4B for linking the billing information associated with the service provision to the user 5 to the identification information to manage, an assistant database 4C for recording a plurality of helpers He together with their characteristic information, and a user identification database 4D for linking at least one of the personal identification number data of the user, the voiceprint collation data, the fingerprint collation data, and the facial image recognition data to the personal information about the user as the user identification data so as to manage accessibly and systematically.

The service-provision robot 6 is preferable to include various variations selectable when the user 5 receives the service. The present embodiment illustrates examples with variations such as a nurse-type service-provision robot 6A for mainly performing the care and assistance for the user 5, a cook-type service-provision robot 6B for mainly performing the provision of food and drink including pouring sake for the user 5, a housekeeper-type service-provision robot 6C for mainly performing the peripheral cleaning of the user 5, a recreation service-provision robot 6D for mainly performing the game match with the user 5, and a special service-provision robot 6E for providing special services such as those performing the walking assistance with being attached to the body of the user 5. Which variation to use is selected depending on the taste and needs of the user 5. It should be noted that the example of variations described in this embodiment is merely an example, and it is obvious that various modifications are conceivable.

Figure 2:
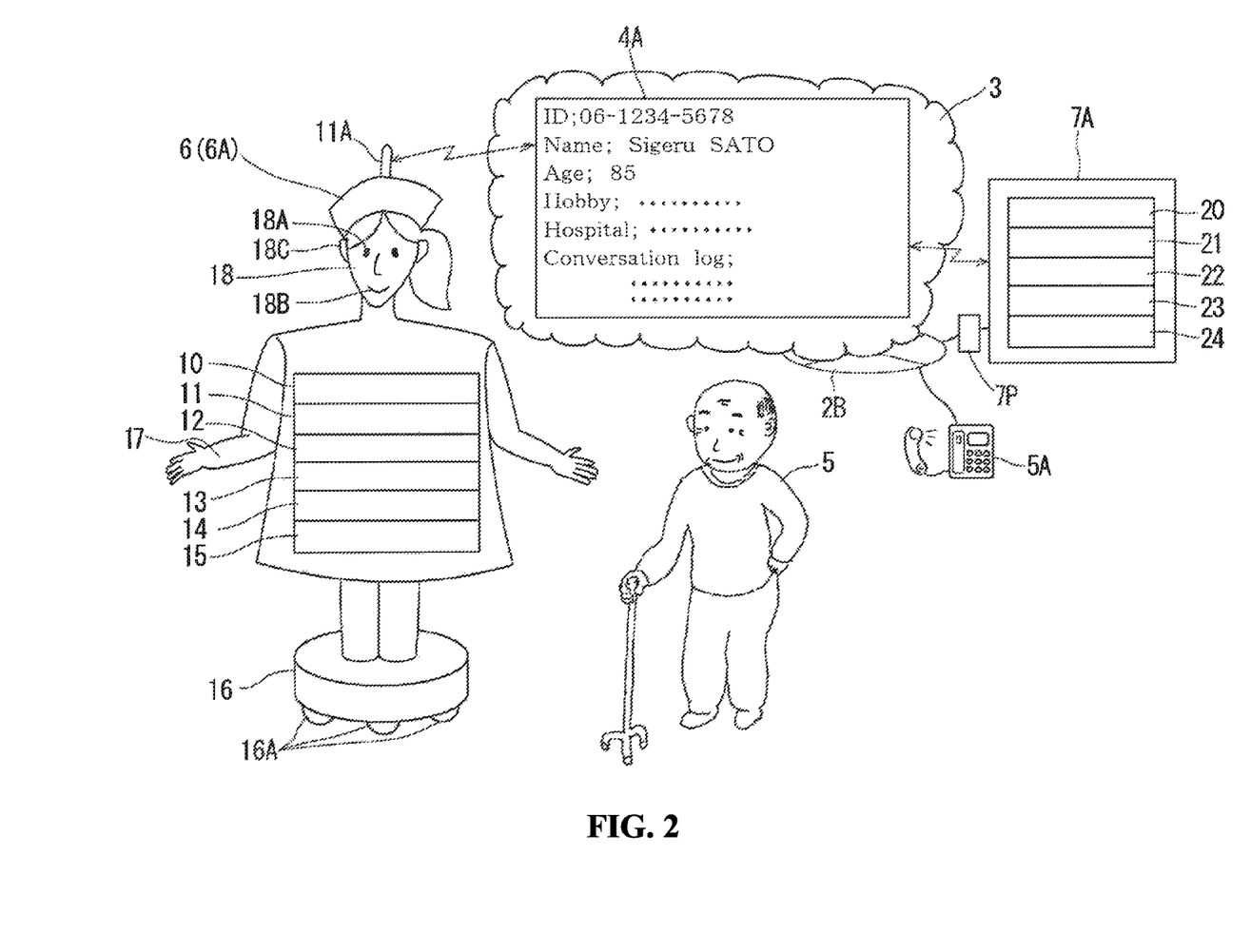
FIG. 2 is a diagram illustrating the configuration and the operation of a service-provision robot and a telephone-service-provision server.

FIG. 2 is a diagram illustrating the configuration of a service-provision robot 6. As illustrated in FIG. 2, the service-provision robot 6 of the present embodiment includes: an identification-information acquisition means 10 configured to acquire the identification information about the user 5 by contact with the user 5; an experience-information search means 11 configured to access to the experience-information database 4A so as to extract the experience information about the user 5 by using the identification information about the user 5; a request identification means 12 configured to identify the request of the user 5 by contact with the user 5; a service provision means 13 configured to provide a service satisfying the request of the user based on the experience information; an experience storage means 14 configured to store the experience information obtained in accordance with the provision of the service into the experience-information database 4A; and a user monitoring report means 15 configured to monitor the service provision to the user 5, and configured to detect the abnormal occurrence at least when the reply of user 5 is delayed beyond the set threshold value so as to report to the medical institution Ho where the user 5 visits. These are constituted by the programs to be executed by the arithmetic processing unit (not shown) in the service-provision robot 6.

The service-provision robot 6 has a function of moving to the home of the user 5 and of moving so as to enable the movement associated with the service provision, and as an example, includes a cart 16 on which the legs of the service-provision robot 6 are mounted and including wheels 16A configured to rotatably move in any direction. It should be noted that the function enabling this movement may be achieved by the actuator and the walking controller included in the legs of the service-provision robot 6 so as to enable the service-provision robot 6 to be a biped.

In addition, the service-provision robot 6A illustrated in FIG. 2 is a nurse-type service-provision robot 6, and therefore as an example of the service, includes arm portions 17 for supporting the body of the user 5 during walking, wiping the body, and performing the bathing assistance, and an actuator not shown in the face 18 for representing the expression. The eye 18A disposed in the face 18 includes a camera for imaging the state of the user 5, the mouth 18B includes a speaker for generating speech, and the ear 18C includes a microphone for collecting the speech of the user 5, and therefore it is what is called a humanoid robot. It should be noted that the present invention is not limited to that all these parts are complete, and it is obvious that these parts are selectively mounted on the service-provision robot 6 as needed.

The identification-information acquisition means 10 performs the image recognition of the image of the user 5's face captured by the eye 18A and the voiceprint recognition of the user 5's speech by using the user identification database 4D to identify the user 5 so as to convert into the identification information. This enables the service-provision robot 6 to acquire the identification information without any particular operation by the user 5. However, it is also possible to acquire the identification information with a read means for reading the ID card of the user 5. Alternatively, it is also possible to identify the user 5 more reliably by the personal identification number with a keyboard or a touch panel for having the user 5 enter the personal identification number. Furthermore, it is also conceivable to obtain the identification information by using the authentication for capturing the biometric characteristic such as the fingerprint authentication and the retina pattern authentication.

The user experience-information search means 11 includes a communication device 11A that performs radio communication for accessing the experience-information database 4A (although the shape of the antenna is illustrated in FIG. 2 for clarity, the form of the communication device 11A is preferably invisible from outside), and is configured to be accessible to the experience information about the user 5 linked to the identification information by accessing the experience-information database 4A in the cloud 3 by using the identification information about the user 5.

The request identification means 12 identifies a request of the user 5 by the analysis of the image of the user 5 imaged by the eye 18A or the speech recognition using the speech signal of the user 5. This enables the user 5 to request the service from the service-provision robot 6 without any particular operation. However, it is obvious that a keyboard or a touch panel for having the user input requirements may be provided.

The service provision means 13 provides services meeting the request, and has a conversation with the user 5 first. It should be noted that the service provision means 13 performs the provision of services by using the experience information about the user 5 acquired by the experience-information search means 11 and the user request. The example illustrated in FIG. 2 includes the name of the user 5 and the information indicating that the user 5 has suffered from knee pain since 2008 as the experience information about the user 5, and shows an example that the service-provision robot 6 says to the user 5, "Mr. Sato, what is the condition of your knee?". Then, the walking assistance service of the user 5 is provided by using the arm portions 17 and the like. The service-provision robot 6 speaks to the user 5 in accordance with the situation of the user 5, and therefore the user 5 can feel the sense of closeness. In addition, the actuator for expressing feelings is provided in the face 18, and for example, when the service-provision robot 6 makes the pronunciation, the robot 6 expresses a smile, a facial expression of worries, and the like, and therefore the user 5 can feel a sense of security and familiarity.

The experience storage means 14 records the event obtained in accordance with the service provision into the experience-information database 4A as the experience information, and records at least the contents of the performed service and its period, the request of the user 5, the contents of the reply and its period, and the like as an event. In the case of this example, the service-provision robot 6 records the contents of the conversation performed with the user 5. In addition, it is preferable to record things related to the experience information about the user 5 (such as medical condition, visit date, history of severe injuries and illnesses, name of the user, the nickname, sex, age, family structure, and tastes) from the contents of the conversation and the like. In the case of this example, the user 5 reports the medical condition called "knee pain when walking", and therefore it is preferable to record this as the experience information.

The user monitoring report means 15 monitors the reaction of the user 5 to the service provision, and includes a timer measured from the service provision point (not shown), and a report means (the communication device 11A is used) for determining the case where the period measured by the timer exceeds the threshold value defined for the contents of the provided services and each user as an abnormal situation so as to report to the contact address recorded as the information in the medical institution. In the case of this example, the period from the point when the service-provision robot 6 talks to the user 5 until the response of the user 5 is measured, the threshold value of the user 5 is appropriately set from the mean value, and when the response from the user 5 is delayed beyond the threshold value, the abnormality is detected to be reported to the medical institution Ho (attending physician, emergency hospital, and the like). At this time, it is preferable to be able to determine the situation more accurately on the medical institution Ho side by, for example, transferring the moving image obtained by imaging the state of the user. It should be noted that the setting of the threshold value may be performed, for example, on any one of the service-provision robot 6 side and the manager (management device) side.

The service-provision robot 6 is preferable to be conveyed together with, for example, the helper He paying a care visit to the user 5 (see FIG. 1), which allows the helper He to cause the service-provision robot 6 to perform the walking assistance and the bathing assistance that relatively require the physical strength, whereby the helper He himself can focus on the light work that needs to be performed by humans.

It should be noted that the management of the provision situation of services to the user 5 is performed by the billing server 8 illustrated in FIG. 1, and more specifically, is performed by counting the points of the service to the user 5 by monitoring the experience information for each user 5 to be stored in the experience-information database 4A. Usually, the points of services defined by the care insurance system and available to the user 5 are defined, periodically the points are added, the management is performed by subtracting the points in accordance with the dispatch of the helper He and the service-provision robot 6, and periodically the utilization certificate 8A is issued. However, the present invention is not limited to those for managing billing information by the points, and can manage the service usage date by the amount of money.

In addition, the monitoring of each service-provision robot 6 by the manager (management device) (for example, the monitoring such that the manager can grasp the trouble when the trouble occurs in the service-provision robot 6) may be performed through the billing server 8 or through other servers and the like.

After the service-provision robot 6 illustrated in FIG. 2 finishes the provision of services to leave the user 5, when the user 5 wants to change the next-time promise, the user can call the telephone number of the service-provision robot 6 told in advance by using the possessed phone (user side terminal) 5A.

The telephone connector 7P provided in the telephone service provision server 7A has a function of receiving the telephone number report of the telephone 5A on the user side by the connection from the telephone network 2B. The reference numerals 20 to 24 denote programs executable by the arithmetic processing unit in the telephone service provision server 7A, and they include an identification information acquisition program 20 of searching the user identification database by using the telephone number of the user 5 when receiving a call through the telephone line to acquire the identification information, an experience information search program 21 of accessing the experience-information database 4A to extract the experience information about the user 5 by using the identification information about the user 5, a conversation program 22 of providing services by the conversation with the user through the telephone line by using the experience information, an experience storage program 23 of storing the experience information obtained in accordance with the provision of services into the experience-information database, and a user monitoring report program 24 of monitoring the conversation with the user 5, of detecting the abnormality occurrence at least when the reply of the user 5 is delayed beyond the set threshold value, and making a report to the medical institution where the user visits.

The identification information acquisition program 20 converts the telephone number obtained through the telephone connector 7P into the identification information about the user 5 (ID). Alternatively, the telephone number itself is set to be the identification information about the user 5. It should be noted that it is also possible to obtain the identification information by asking the user 5 to say a password to check the user 5, and to identify the user 5 by the voiceprint analysis of the user 5.

Then, the experience information search program 21 receives the personal information linked to the identification information about the user 5 by searching the experience-information database 4A by using the identification information, and the conversation program 22 provides services of having a conversation with the user 5 by using the experience information about the user 5. Here, before the use of the experience information about the user 5, the service-provision robot 6A can have a conversation in consideration of the experience obtained at the time of providing services to the user 5 in the speech of the service-provision robot 6A.

In the example illustrated in FIG. 2, the information remains that the knee has a little pain when walking, and therefore in accordance with this, the service-provision robot 6A can have a conversation, for example, "Since then, is the pain of your knee getting better?" and the like. The user 5 has a conversation by telephone with the contents following the conversation previously made with the service-provision robot 6A, and therefore can obtain a sense of closeness, and can have a sense of satisfaction as if the user 5 monopolizes the service-provision robot 6A.

The experience storage program 23 also stores the experience information obtained by the conversation program 22 into the experience-information database 4A. This allows the provision of services to reflect the conversation by telephone next time the service-provision robot 6A visits the user 5. In addition, the experience-information database 4A is updated only by the user 5 making a conversation using the telephone (user side terminal) 5A, and therefore, for example, the user 5 can easily change the next visit promise date.

The user monitoring report program 24 monitors the services to be supplied to the user 5 by using the experience-information database 4A, and when the reaction of the user 5 is delayed beyond the threshold value, detects an abnormality to report to the medical institution Ho. As a result, the abnormal situation that occurs in the user 5 during the call can be quickly dealt with.

Figure 3:
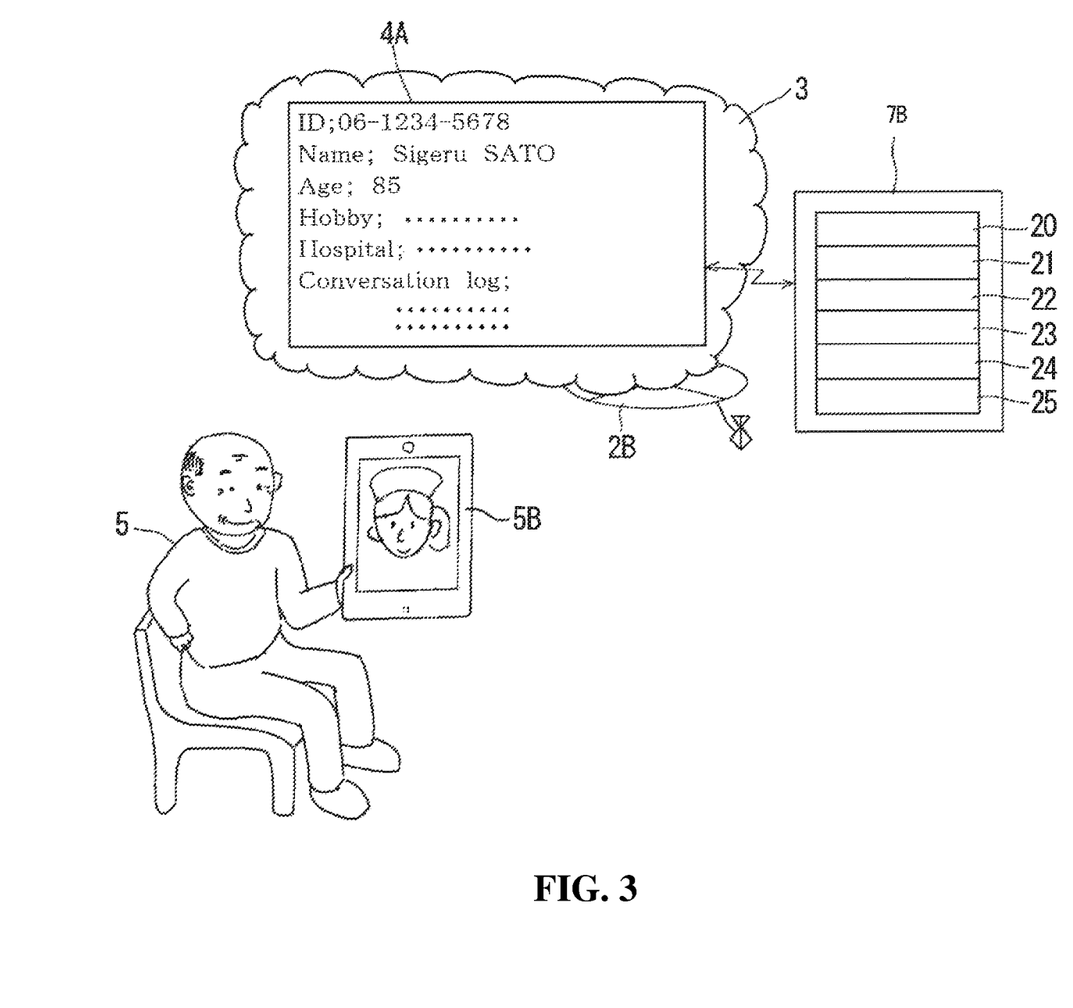
FIG. 3 is a diagram illustrating the configuration and the operation of a net-service-provision server.

FIG. 3 is a diagram illustrating the configuration and the operation of the net-service-provision server 7B, and the net-service-provision server 7B illustrated in this example can be shared by the same server 7 as the telephone service provision server 7A. In addition, the net-service-provision server 7B is connected to the telephone network 2B and the Internet (not shown) to be communicatively connected to the portable information terminal on the user side (user side terminal) 5B and the cloud 3.

The reference numeral 25 denotes a display program executed by the arithmetic processing unit in the net-service-provision server 7B, and although other programs 20 to 24 are approximately the same as those described previously, it is conceivable that the identification information acquisition program 20 obtains the IP address and the physical address of the portable information terminal 5B from the packet and header information received from the portable information terminal 5B to obtain the identification information for identifying the user 5 by using the packet and header information.

Now, when the user 5 connects to the network-service-provision server 7B by using the mobile information terminal 5B, the net-service-provision server 7B acquires the identification information about the user 5, searches the experience-information database 4A for the experience information about the user 5 linked to the identification information, and displays the image of the service-provision robot 6A drawn based on the experience information and selected by the taste of the user 5.

The user has a conversation while watching the screen of the service-provision robot 6A displayed on the mobile information terminal 5B, thereby allowed to obtain a sense of satisfaction as if the user monopolizes the service-provision robot 6A all the time. In addition, the experience-information database 4A is updated also by the conversation through the portable information terminal 5B, and therefore, for example, the user 5 can easily change the next visit promise date and the like.

Figure 4:
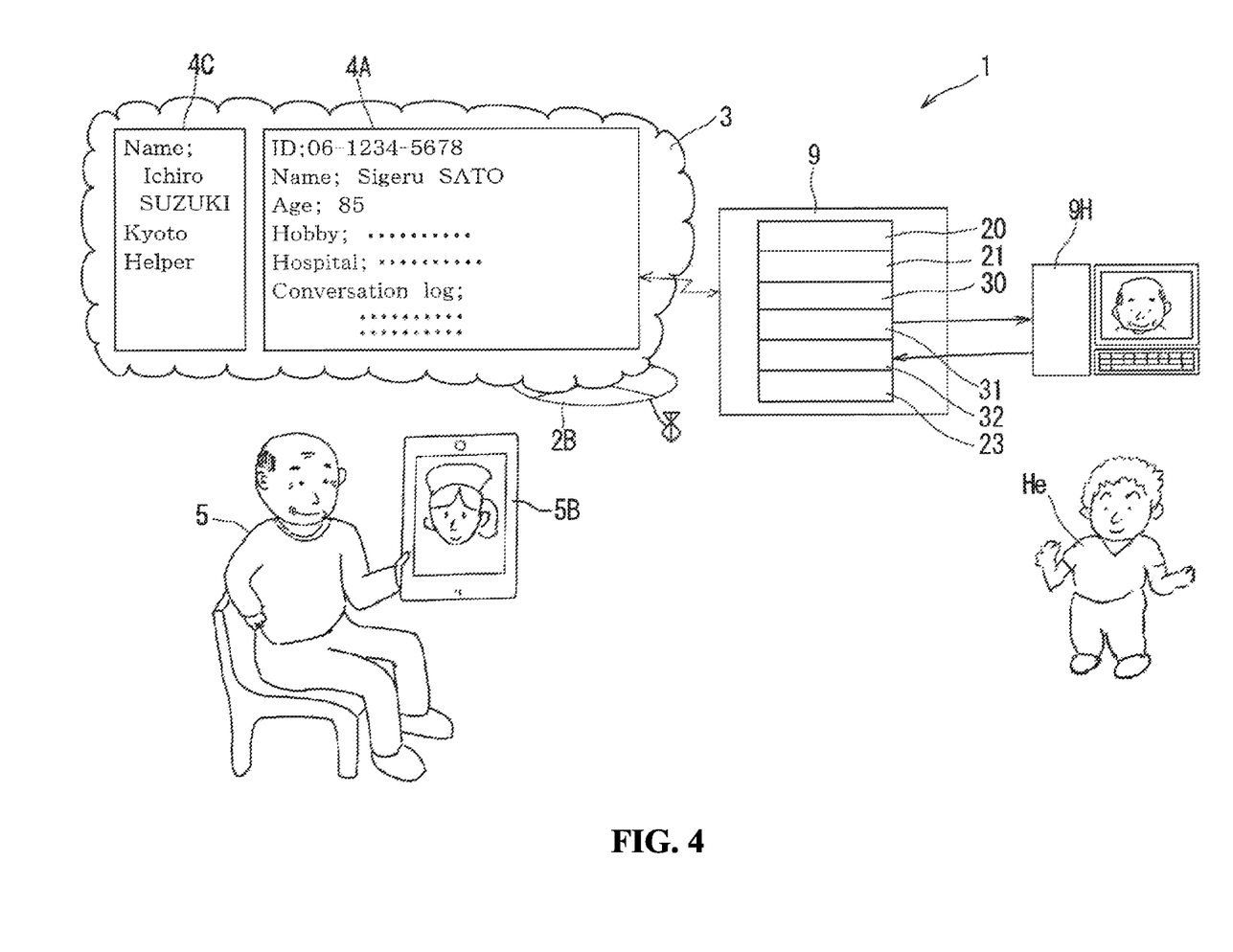
FIG. 4 is a diagram illustrating the configuration and the operation of a remote-service-provision server.

FIG. 4 is a diagram illustrating the configuration and the operation of a remote-service-provision server 9 for performing the remote service provision by the helper He.

In FIG. 4, any one of the reference numerals 20 to 23 and 30 to 32 denotes a program configured to be executable by the arithmetic processing unit in the remote service provision server 9, the reference numeral 30 denotes an assistant selection program for selecting the optimal helper He for the user 5 by accessing the assistant database 4C, the reference numeral 31 denotes a personal information transmission program for transmitting the personal information about the user 5 to only the terminal 9H possessed by the selected helper He, and the reference numeral 32 denotes an audio image conversion transmission program for converting the audio information and/or image information input via the terminal 9H on the helper He side into the tone and/or the image of the service-provision robot 6A to subsequently transmit to the user. It should be noted that the programs 20 to 23 are substantially the same as those already described, and therefore the description thereof will be omitted.

In the case of this example, when the user connects to the remote service provision server 9 by using the portable information terminal 5B and the like, the assistant selection program 30 accesses the experience-information database 4A and the assistant database 4C in the cloud 3, selects the optimal helper He from the list of helpers He during standby by using the hometown and tastes of the user 5 from the experience information about the user 5 linked to the identification information about the user 5, and connects to the terminal 9H possessed by the helper He.

Then, the personal information transmission program 31 extracts the video obtained by imaging the user 5 and the speech of the user 5 obtained from the terminal of the user 5B, and only the information about the user 5B from the experience-information database 4A so as to cause the terminal 9H on the helper He side to display in a browsable manner. As a result, the helper He can understand what the user 5 requests by knowing the current state of the user 5 by using the displayed contents on the terminal 9H and can have a conversation including the experience information in a remote location.

The audio image conversion transmission program converts the image of the imaged helper He and the collected speech by the terminal 9 on the helper He side into the image and the speech of the service-provision robot 6A selected based on the taste of the user 5 so as to transmit to the terminal 5B on the user 5 side. This allows the user 5 to have a conversation with the helper He while feeling as if talking with the service-provision robot 6A.

In the case of this example, the helper He can check the situation of the user 5 and perform an accurate dialogue, and therefore can provide more careful and natural services. In addition, the helper He is selected so as to suit the user 5, and therefore for example, a unique dialect uttered by an aged person can be caught by a helper He from the same rural area. Furthermore, the number of times and the like of the dialogue with the user 5 is integrated to be recorded into the assistant database 4C, whereby the helper He can also be selected depending on the number of times of contact with the user 5.

The above-described example is just one example for the description of the present invention, and it is obvious that various modifications are possible.

For example, the service-provision robot 6 is not limited to a humanoid robot, and may be such a thing as worn on the body of the user 5 for supporting a part of the joints of the user as illustrated by the reference numeral 6E in FIG. 1.

In addition, it is also conceivable that the service-provision robot 6 is disposed in stores and facilities such as a bar and a game center to be used for serving customers, attracting customers, and the like.

In any case, the user 5 can receive the provision of services by the service-provision robot 6 without performing complicated operations at all, and can feel a sense of closeness to the service-provision robot 6. On the other hand, for the helper He on the side of providing services, the fatigue with the helper can be minimized by causing the service-provision robot 6 to perform the work to be a hard work when performing the care and assistance for the user 5. In addition, the higher the performance becomes, the more expensive the service-provision robot 6 becomes; however, the service-provision robot 6 can be shared by a large number of users 5, and therefore the cost of each user 5 can be reduced by that amount.

DESCRIPTION OF THE SIGN 1 service provision system
3 cloud
4A experience-information database
4B billing database
4C assistant database
4D identification database
5 user
5A, 5B user side terminal
6 service-provision robot
7A telephone service provision server
7B net service provision server
8 billing server
9 remote service provision server
9H terminal on the assistant
10 identification-information acquisition means
11 experience-information search means
12 request identification means
13 service provision means
14 experience storage means
15 user monitoring report means
20 identification information acquisition program
21 experience information search program
22 conversation program
23 experience storage program
24 user monitoring report program
25 display program
30 assistant selection program
31 personal information transmission program
32 audio image conversion transmission program
33 experience storage program
He assistant
Ho medical institution

The invention claimed is:

1. A service-provision management system comprising:
an experience-information database configured to link experience information about a plurality of users to identification information about each of the users to be managed;
a service-provision robot including one or more processors configured to provide a service for each of the users, configured to acquire the identification information about each of the users, configured to access the experience-information database so as to extract the experience information about each of the users by using the identification information about each of the users, configured to identify a request of each of the users, configured to provide the service satisfying the request of each of the users based on the experience information, and configured to store the experience information obtained in accordance with a provision of the service into the experience-information database;
an assistant database for recording characteristic information of a plurality of assistants;
a terminal on an assistant side operable by each of the plurality of assistants;
a remote service provision server configured to execute an assistant selection program for searching the assistant database to select an assistant when receiving the request from each of the users;
a personal information transmission program capable of transmitting at least one of a speech and/or an image of each of the users, the experience information about each of the users, and the request to the terminal of the selected assistant;

a speech and image conversion transmission program for converting speech information and image information including facial expressions and movements of the selected assistant entered through the terminal on the assistant side into a tone and an image of the service-provision robot to be subsequently transmitted to each of the users, such that each of the users can feel a same feeling although the selected assistant is changed; and an experience storage program for storing input information about service provision contents by the selected assistant into the experience-information database as the experience information.

2. The service-provision management system according to claim 1, further comprising:

a billing database configured to link billing information, in accordance with a service provision to each of the users, to the identification information so as to manage; and a billing server on a manager side configured to access the billing database to extract the billing information, wherein the service-provision robot or the billing server is configured to store a billing record for the service provision into the billing database.

3. The service-provision management system according to claim 1, wherein the service-provision robot imitates a person's appearance selected by tastes of each of the users, and the experience information includes taste information indicating the tastes of each of the users.

4. The service-provision management system according to claim 1, wherein the service includes at least one of a conversation with each of the users, a care for each of the users, an assistance for each of the users, a game match with each of the users, and a provision of food and drink to each of the users.

5. The service-provision management system according to claim 1, wherein the service-provision robot has a function of expressing its feelings.

6. The service-provision management system according to claim 1, wherein the service-provision robot has a function of movement.

7. The service-provision management system according to claim 1, further comprising:

a user identification database configured to link at least one of a personal identification number data, a voiceprint verification data, a fingerprint matching data, and a facial image recognition data of each of the users to personal information about each of the users as a user identification data to be accessibly and systematically managed, wherein the service-provision robot is configured to access the user identification database to acquire the identification information about each of the users.

8. The service-provision management system according to claim 7, further comprising:

a telephone service provision server on a manager side configured to enable a speech communication and a telephone number communication from a telephone on an user side through a telephone line, wherein the user identification database associates a telephone number of each of the users with personal information about each of the users to manage accessibly and systematically, and the telephone service provision server executes an identification information acquisition program for searching the user identification database by using the telephone number of each of the users when receiving a call through the telephone line to acquire identification information, an experience information search program for accessing the experience-information database to extract the experience information about each of the users by using the identification information about each of the users, a conversation program for performing the provision of the service by a conversation with each of the users through the telephone line by using the experience information, and an experience storage program for storing the experience information obtained with the provision of the service into the experience-information database.

9. The service-provision management system according to claim 1, further comprising:

a net service provision server on a manager side configured to enable a connection from a terminal on a user side through the Internet, wherein the net service provision server executes a display program for displaying the image imitating the service-provision robot on the user side terminal by the connection from the user side terminal through the Internet, an identification information acquisition program for acquiring the identification information about each of the users through the user side terminal, an experience information search program for extracting the experience information about each of the users from the experience-information database by using the identification information about each of the users, a conversation program for performing the provision of the service by conversation through the terminal on the user side by using the experience information, and an experience storage program for storing the experience information obtained with the provision of the service into the experience-information database.

10. The service-provision management system according to claim 1, wherein information about a medical institution where each of the users visits is recorded in the experience-information database, and the service-provision management system is configured to monitor the service provision for each of the users and detect an abnormality occurrence so as to report to the medical institution where each of the users visits when at least one response of each of the users is delayed.

* * * * *